United States Patent
Voss

(10) Patent No.: US 6,175,039 B1
(45) Date of Patent: Jan. 16, 2001

(54) ACETIC ACID REACTIVE DISTILLATION PROCESS BASED ON DME/METHANOL CARBONYLATION

(75) Inventor: Bodil Voss, Virum (DK)

(73) Assignee: Haldor Topsoe A/S, Lyngby (DK)

(*) Notice: Under 35 U.S.C. 154(b), the term of this patent shall be extended for 0 days.

(21) Appl. No.: 09/365,202

(22) Filed: Aug. 2, 1999

Related U.S. Application Data

(60) Provisional application No. 60/095,457, filed on Aug. 6, 1998.

(51) Int. Cl.[7] .................................................. C07C 51/12
(52) U.S. Cl. ............................................. 562/519; 562/607
(58) Field of Search ...................................... 562/519, 607

(56) References Cited

U.S. PATENT DOCUMENTS 4,994,608 * 2/1991 Torrence et al. .
5,334,755 * 8/1994 Yoneda et al. .
5,502,243 * 3/1996 Waller et al. .
5,831,120 * 11/1998 Watson et al. .

FOREIGN PATENT DOCUMENTS 055618   7/1982   (EP) .
161874   11/1985  (EP) .
250189   12/1987  (EP) .

* cited by examiner

*Primary Examiner*—James O. Wilson
*Assistant Examiner*—Robert W. Deemie
(74) *Attorney, Agent, or Firm*—Ostrolenk, Faber, Gerb & Soffen, LLP

(57) ABSTRACT

A process for the production and purification of acetic acid by carbonylation of methanol, DME or reactive derivatives thereof in a distillation column containing a homogenous catalyst system.

4 Claims, 1 Drawing Sheet

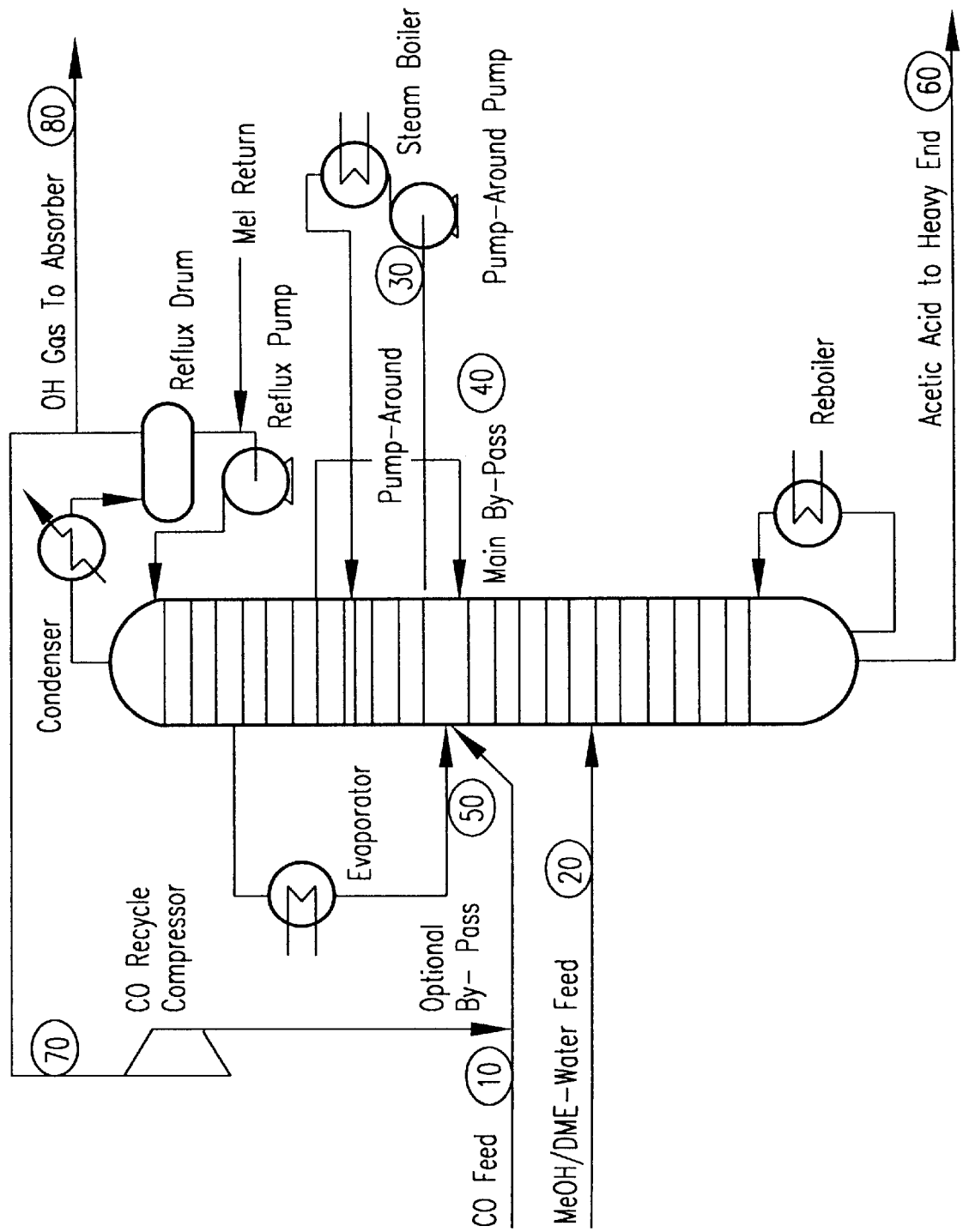

ACETIC ACID REACTIVE DISTILLATION PROCESS BASED ON DME/METHANOL CARBONYLATION

This application claims the benefit of U.S. Provisional Application Ser. No. 60/095,457, filed on Aug. 6, 1998.

BACKGROUND OF THE INVENTION

1. Field of the Invention

This invention is directed to a method of producing acetic acid by a reactive distillation process from carbonylation of methanol (MeOH) and/or dimethylether (DME).

The invention concerns in particular improved production of acetic acid from methanol, DME or a combination of these components over a homogeneous catalyst system contained in a distillation column.

The catalyst may be any homogeneous carbonylation catalyst which is soluble in the reaction medium.

2. Description of the Related Art

Conventional acetic acid synthesis is performed in a homogeneous process, where methanol is carbonylated in a liquid, catalytic medium contained in a stirred reactor. Methanol derivatives such as methyl acetate and dimethyl ether may be applied instead of or in combination with methanol. Carbon monoxide reactant is typically introduced at bottom of the reactor and distributed in the liquid. The catalyst system comprises one or more Group VIII metal compounds, preferably rhodium or iridium and a halide promoter, e.g. methyl iodide (MeI).

Beside primary reaction (1) other reactions are taking place in the reaction medium. The most predominant are:

  (1)

  (2)

  (3)

  (4)

  (5)

Also small amounts of higher acids, primarily propanoic acid, is synthesized in the process.

The presence of water is essential to stabilize the catalyst system. So-called stabilizers can be added to the reaction medium in order to reduce the water concentration. A surplus of CO is required to keep the catalyst system activated and unreacted CO gas is purged from the liquid reaction medium at top of the reactor. CO gas (+inerts and hydrogen synthesized by reaction (2)) stream drives off a fraction of volatile components from the liquid, which is recovered and recycled back to the reaction section.

The acetic acid product is recovered in a liquid product stream from the reactor and separated by flash off from the catalyst containing reaction medium in a down-stream flash vessel operating at a pressure lower than the reactor pressure, typically at about 1–2 bar. The liquid from the flash vessel containing the group VIII metal catalyst is recycled to the reactor by means of pumping.

As acetic acid is the least volatile major compound in the flash medium, the recovery of the acetic acid produced unavoidably leads to the undesired flash off of more volatile components also contained in the flash medium such as water, methyl iodide, methyl acetate, hydrogen iodide and unconverted methanol and dimethyl ether.

In order to recover these components from the product down stream the reaction section, they are separated in several distillation columns and absorbers and returned to the reaction section.

The downstream separation process comprises essentially three steps.

1. Primarily methyl iodide and hydrogen iodide are recovered in a light end column and returned to the reactor.
2. Primarily water, methyl acetate, and remaining methyl iodide and hydrogen iodide are recovered in a dehydration column and returned to the reactor.
3. Primarily propanoic acid and a fraction of acetic acid is withdrawn from the bottom of a heavy end column, in which also the product acetic acid is recovered.

Various overhead gases are separated from methyl iodide in an absorption system.

In the dehydration column, hydrogen iodide is formed continuously by hydrolysis of methyl iodide (eq. 4) Eventually, this leads to the formation of a hydrogen iodide/water/acetic acid azeotrope. This azeotrope may be dissociated by addition of small amounts of methanol to the dehydration column.

Essentially, the resulting component effluents from the acetic acid synthesis and purification sections are unconverted carbon monoxide (+gases) and the product acetic acid (+byproducts).

The fact that acetic acid is the least volatile major component in the reaction mixture declines the process economy because of energy consumption and investment in the conventional process layout.

SUMMARY OF THE INVENTION

In the process of the present invention the less volatile acetic acid is withdrawn at bottom of the distillation column, while unreacted CO is withdrawn at top of the column. The remaining reactants in the synthesis, or the products at the present chemical equilibria, are remained inside a distillation tower providing simultaneous production and purification of acetic acid product within a distillation column. Accordingly, this invention is a process for the production of acetic acid comprising the steps of (a) carbonylation of methanol, DME or reactive derivatives thereof in a homogenous catalyst containing solution active in the carbonylation;

(b) at the same time collecting the components taking part in present reactions and stripping off mainly unconverted carbon monoxide, hydrogen and inert gases, leaving the remaining components taking part in present reactions; and (c) at the same time as (b) distilling off the acetic acid product from at least part of the remaining components taking part in present reactions, and resupplying the remaining components taking part in present reactions thus reduced in acetic acid to the carbonylation step.

An advantage of the present invention is that the acetic acid product is efficiently removed from the reaction zone in the reactive distillation process utilizing its low volatility.

BRIEF DESCRIPTION OF THE DRAWING

The invention is described in greater detail in the following description by reference to the drawing, which shows the flow of a specific embodiment of the invention.

DETAILED DESCRIPTION OF THE PREFERRED EMBODIMENT

Referring to the drawing, the span of trays carrying catalyst containing liquid is referred to as reaction zone. The catalyst, which is dissolved in the reaction medium, is prevented from escaping the reaction zone by means of a total pump-around: All the liquid arriving at the bottom of the reaction zone is withdrawn (stream 30) and returned to a higher tray level.

The tray underneath the reaction zone is fed by liquid (main bypass stream 40) from a tray above the reaction zone. An optional stream 50 (bypass 2) richer in water than stream 40 departing from a tray above that of the main bypass stream 40 serves to maintain the desired water concentration in the reaction zone. Stream 50 is evaporated, such that the water enrichment is performed in the reaction zone and not in the acetic acid rectification part below the reaction zone.

The condenser at top of the column reduces purge of highly volatile methyl iodide.

The span of trays below the reaction zone to separate acetic acid and higher acids from the remaining components.

Carbon monoxide and the oxygenate feeds are both introduced below the reaction zone. When the reactants pass the catalyst containing span of trays, they are converted into acetic acid. A surplus of the carbon monoxide serves to maintain an adequate carbon monoxide pressure over the catalyst liquid and further to carrying the vaporized synthesized product (and other components formed of liquid equilibrium reactions) upwardly in the column from the reaction zone. Carbon monoxide is withdrawn at top of the column together with small amounts of essentially methyl iodide. The remaining components are withdrawn in a liquid stream (main by-pass 1, stream 40) and sent to the lower part of the column. In the lower part of the column the acetic acid (stream 60) is withdrawn together with higher acids, while the components with higher volatility are flowing up through the reaction zone of the column.

From the top of the column a split stream (stream 70) of the unconverted carbon monoxide is optionally sent via a recycle compressor and mixed with carbon monoxide make-up (stream 10). Carbon monoxide purge (stream 80) is purified from methyl iodide in an absorber, and the methyl iodide is returned to the distillation column.

From the bottom of the column, the higher acid containing acetic acid (stream 60) may be sent to a so-called heavy end column as in the conventional layout.

The column is operated at 25–40 kg/cm$^2$. The temperature in the column is in the range 150–280 EC in the reaction zone and the lower part of the column, whereas in the upper part of the column the operation temperature range is from condenser temperature to about 200 EC.

The molar ratios of stream 10 and 20 may be 1.2:1–2:1. The molar ratio of stream 10 and 70 admixture should be at a value providing a partial pressure of carbon monoxide of at least 1 kg/cm$^2$, preferably above 5 kg/cm$^2$ in the reaction zone of the column. The molar ratio between the combined streams 10 and 70 to the combined streams 20, 40 and 50 is in the range 0.5:1–3:1. The molar ratio between stream 30 and the combined streams 10, 20, 40, 50 and 70 is in the range 0.5:1–2:1.

The molar ratio between stream 40 and stream 60 is 2:1 to 10:1.

The heat of reaction from the highly exothermic process is removed and e.g. recovered in a steam boiler heated by the pump-around stream (stream 30).

As an advantage of the present invention, the reactive distillation column replaces several operation units of the conventional layout, such as stirred carbonylation reactor, flasher, light end column, dehydration column, LP absorber, pumps and pipes.

As another advantage of the present invention the catalyst solution contrary to the known processes is not subjected to a flash vaporization. The flash operation, as carried out in the conventional process, leads to a considerable reduction in CO partial pressure rendering the catalyst subject to inactivation and precipitation as described e.g. in EP 55,618, 161,874 and 250,189.

The flash-evaporation of the conventional layout may also lead to mist formation in the flash vessel, whereby small catalyst containing droplets, which are carried over to the distillation system down-stream. Thus, the process of the present invention eliminates the loss of catalyst associated with flash vaporization.

It is essential to the process economy to keep the rhodium catalyst loss at a minimum, as rhodium is costly.

A further advantage of the present invention is that hydrogen iodide will not accumulate in the column, because the oxygenate feed (stream 20) is introduced to the distillation column at a stage eliminating the critical water limit of the column at which the hydrogen iodide is normally accumulated, due to the dissociation induced azeotrope. By introducing the oxygenate feed stream at a number of trays below the reaction zone, hydrogen iodide is efficiently converted into methyl iodide in the presence of methanol.

If the demand on water concentration is low, the internal liquid flow and carbon monoxide flow rates are relatively low.

If the demand on the water concentration is high, a large CO recycle is required, and a secondary bypass stream richer in water than bypass 1, which is evaporated bypass 2 (stream 50) is introduced beneficially. The number of trays below the reaction zone must be increased accordingly in order to obtain proper separation.

At high internal flow rates, a net heat supply of about 0.8 Gcal/MT HOAc is required (which is similar to the equivalent range of the conventional acetic acid synthesis), while at low internal flow rates, the net heat requirements are considerably reduced or even slightly negative.

What is claimed is:

1. A process for the production of acetic acid comprising the steps of
    (a) carbonylation of methanol, dimethylether or reactive derivatives thereof in a homogenous catalyst containing solution active in the carbonylation;
    (b) at the same time collecting, in a distillation column at the same pressure, the components taking part in present reactions and stripping off mainly unconverted carbon monoxide, hydrogen and inert gases, leaving the remaining components taking part in present reactions; and
    (c) at the same time as (b) distilling off the acetic acid product from at least part of the remaining components taking part in present reactions, and resupplying the remaining components talking part in present reactions thus reduced in acetic acid to the carbonylation step.

2. A process as recited in claim 1, wherein the simultaneous steps (b) and (c) are carried out at the same pressure level as (a).

3. A process as recited in claim 2, wherein the simultaneous steps are conducted within a distillation column.

4. A process as recited in claim 1, wherein the catalyst system comprises at least one element of Group VIII metal compounds.

* * * * *